(12) United States Patent
Reah et al.

(10) Patent No.: US 12,090,063 B2
(45) Date of Patent: Sep. 17, 2024

(54) INTERVERTEBRAL IMPLANTS

(71) Applicant: AXIS SPINE TECHNOLOGIES LTD, St. Albans (GB)

(72) Inventors: Christopher Reah, St. Albans (GB); Jonathan Arcos, St. Albans (GB); Nicholas Sandham, London (GB); David Powell, London (GB); John Sutcliffe, Chelmsford (GB); Patrick McKenna, Stratfield Saye (GB)

(73) Assignee: AXIS SPINE TECHNOLOGIES LTD, St. Albans (GB)

( * ) Notice: Subject to any disclaimer, the term of this patent is extended or adjusted under 35 U.S.C. 154(b) by 658 days.

(21) Appl. No.: 17/294,684

(22) PCT Filed: Nov. 19, 2019

(86) PCT No.: PCT/GB2019/053277
§ 371 (c)(1),
(2) Date: May 17, 2021

(87) PCT Pub. No.: WO2020/104792
PCT Pub. Date: May 28, 2020

(65) Prior Publication Data
US 2022/0015921 A1 Jan. 20, 2022

(30) Foreign Application Priority Data

Nov. 19, 2018 (GB) ...................... 1818850

(51) Int. Cl.
*A61F 2/44* (2006.01)
*A61F 2/30* (2006.01)
*A61F 2/46* (2006.01)

(52) U.S. Cl.
CPC .......... *A61F 2/447* (2013.01); *A61F 2/30771* (2013.01); *A61F 2/4601* (2013.01);
(Continued)

(58) Field of Classification Search
CPC .... A61F 2/447; A61F 2/30771; A61F 2/4601; A61F 2002/30266; A61F 2002/30505;
(Continued)

(56) References Cited

U.S. PATENT DOCUMENTS

| | | | |
|---|---|---|---|
| 6,045,579 | A | 4/2000 | Hochshuler et al. |
| 6,102,950 | A | 8/2000 | Vaccaro |

(Continued)

FOREIGN PATENT DOCUMENTS

| | | |
|---|---|---|
| EP | 2719360 | 4/2014 |
| WO | 2013184946 | 12/2013 |
| WO | 2014093136 | 6/2014 |

OTHER PUBLICATIONS

Product Brochure "Aero-LL Lateral Lumbar Interbody and Fixation System", Stryker Spine, 2016, pp. 1-52.
(Continued)

*Primary Examiner* — Jessica Weiss
(74) *Attorney, Agent, or Firm* — LIU & LIU

(57) ABSTRACT

The present invention relates to an intervertebral fusion device (10) comprising a superior component (12), an inferior component (14) and a core component (16). The superior component (12) and the inferior component (14) are receivable in an intervertebral space between first and second vertebrae with the core component (16) insertable between the superior and inferior components to determine a separation between the superior and inferior components. A bone graft conveying aperture is defined in at least one of a superior component top surface (18) of the superior component and an inferior component bottom surface (20) of the inferior component. The core component defines a bone graft material holding space which is enclosed except at at least one of a core component top surface and core component bottom surface of the core component and a bone graft material delivery opening. The bone graft mate-
(Continued)

rial delivery opening extends from outside the core component side to the bone graft material holding space. The bone graft material delivery opening is closed by a closure component.

22 Claims, 4 Drawing Sheets

(52) U.S. Cl.
CPC ............ *A61F 2002/30266* (2013.01); *A61F 2002/30505* (2013.01); *A61F 2002/30593* (2013.01); *A61F 2002/30784* (2013.01); *A61F 2002/30841* (2013.01); *A61F 2310/00179* (2013.01)

(58) Field of Classification Search
CPC .. A61F 2002/30593; A61F 2002/30784; A61F 2002/30841; A61F 2310/00179
USPC .............................. 623/17.11–17.16; 606/99
See application file for complete search history.

(56) References Cited

U.S. PATENT DOCUMENTS

| | | |
|---|---|---|
| 6,113,637 A | 9/2000 | Gill et al. |
| 8,308,804 B2 | 11/2012 | Krueger |
| 8,388,686 B2 | 3/2013 | Aebi et al. |
| 9,402,739 B2 | 8/2016 | Weiman et al. |
| 9,526,628 B2 | 12/2016 | Krueger |
| 9,585,765 B2 | 3/2017 | Niemiec et al. |
| 9,801,734 B1 | 10/2017 | Stein et al. |
| 2002/0099444 A1* | 7/2002 | Boyd .................... A61F 2/4455 623/23.76 |
| 2002/0143399 A1 | 10/2002 | Sutcliffe |
| 2004/0254644 A1 | 12/2004 | Taylor |
| 2005/0049707 A1* | 3/2005 | Ferree ................ A61B 17/8811 623/908 |
| 2006/0015183 A1 | 1/2006 | Gilbert et al. |
| 2007/0270957 A1 | 11/2007 | Heinz |
| 2007/0276498 A1 | 11/2007 | Aebi et al. |
| 2008/0294260 A1 | 11/2008 | Gray |
| 2009/0222095 A1* | 9/2009 | Johansonn ............ A61F 2/4611 623/17.16 |
| 2011/0153020 A1 | 6/2011 | Abdelgany et al. |
| 2011/0184522 A1* | 7/2011 | Melkent .................. A61F 2/447 623/17.16 |
| 2013/0006357 A1* | 1/2013 | Krueger .................... A61F 2/44 623/17.13 |
| 2013/0085573 A1 | 4/2013 | Lemoine et al. |
| 2013/0103153 A1 | 4/2013 | Blackwell et al. |
| 2013/0158667 A1 | 6/2013 | Tabor et al. |
| 2015/0164494 A1 | 6/2015 | Glazer |
| 2015/0320568 A1* | 11/2015 | Ameil .................. A61F 2/4455 623/17.13 |
| 2016/0116396 A1 | 4/2016 | Hunt et al. |
| 2016/0166396 A1 | 6/2016 | McClintock |
| 2016/0213483 A1 | 7/2016 | To et al. |
| 2017/0239063 A1* | 8/2017 | Predick .................. A61F 2/447 |
| 2018/0000606 A1 | 1/2018 | Hessler et al. |
| 2018/0036141 A1 | 2/2018 | O'Neil et al. |
| 2018/0098860 A1 | 4/2018 | To et al. |
| 2018/0256357 A1 | 9/2018 | To et al. |

OTHER PUBLICATIONS

International Search Report of Counterpart PCT International Application No. PCT/GB2019/053273.
International Search Report of Counterpart PCT International Application No. PCT/GB2019/053275.
International Search Report of Counterpart PCT International Application No. PCT/GB2019/053277.

* cited by examiner

INTERVERTEBRAL IMPLANTS

FIELD OF THE INVENTION

The present invention relates to intervertebral devices and more specifically to intervertebral fusion devices.

BACKGROUND TO THE INVENTION

Adjacent vertebrae in the spinal column are coupled to each other by an intervertebral disc. The intervertebral disc holds the adjacent vertebrae together and functions as a cushion between the vertebrae whilst allowing for relative movement of the vertebrae. Problems with intervertebral discs arise from one or more of a range of diseases and conditions. A surgical procedure called spinal fusion may be used to address such problems. A typical spinal fusion procedure involves partial or full removal of a problematic intervertebral disc and installation of an intervertebral device in the place of the partially or fully removed intervertebral disc.

Fusion of an installed intervertebral device with the adjacent vertebrae is promoted by appropriate preparation of the vertebrae and the endplates of the intervertebral device. Further to this, bone graft material is often used to promote fusion. A first approach involves packing the intervertebral device with bone graft material before installation of the intervertebral device between the vertebrae. However, it is often difficult in this approach to fill space between an endplate of the intervertebral device and the adjacent vertebra with sufficient and properly placed bone graft material to provide for efficient and robust fusion. A second approach involves installing the intervertebral device between the vertebrae before bone graft material is injected into and/or around the intervertebral device. The first and second approaches may both be used during a spinal fusion procedure. Intervertebral devices configured for injection of bone graft material into the intervertebral device when in situ are known.

The present inventors have become appreciative of shortcomings of known intervertebral devices which are configured for injection of bone graft material in situ. The present invention has been devised in light of the inventors' appreciation of such shortcomings. It is therefore an object for the present invention to provide an improved intervertebral device and more specifically an improved intervertebral fusion device.

STATEMENT OF INVENTION

According to a first aspect of the present invention there is provided an intervertebral fusion device comprising:
  a superior component configured to be received in an intervertebral space between first and second vertebrae whereby a superior component top surface of the superior component abuts against the first vertebra;
  an inferior component configured to be received in the intervertebral space whereby an inferior component bottom surface of the inferior component abuts against the second vertebra, a bone graft conveying aperture being defined in at least one of the superior component top surface and the inferior component bottom surface;
  a core component having a core component top surface, a core component bottom surface and a core component side extending therebetween, the core component configured to be received between the superior and inferior components to determine a separation therebetween, a side boundary of the intervertebral fusion device, which extends between the superior component top surface and the inferior component bottom surface and which defines a perimeter of the intervertebral fusion device, being defined by the superior and inferior components and the core component when the core component is received between the superior and inferior components; and
  a closure component, wherein:
  the core component defines a bone graft material holding space which is enclosed except at at least one of the core component top and bottom surfaces and a bone graft material delivery opening, a holding space opening in at least one of the core component top and bottom surfaces providing for fluid communication between the bone graft material holding space and the at least one bone graft conveying aperture when the core component is received between the superior and inferior components;
  the bone graft material delivery opening extends through the core component side from outside the side boundary to the bone graft material holding space, the closure component being configured to close the bone graft material delivery opening; and
  the core component engages with each of the superior and inferior components to resist ejection of bone graft material from the bone graft material holding space through the side boundary when the bone graft material delivery opening is closed by the closure component and while bone graft material is ejected through the at least one bone graft conveying aperture.

The intervertebral fusion device comprises three main components, namely a superior component, an inferior component, a core component and a closure component. In use, the superior and inferior components are placed in an intervertebral space between first and second vertebrae formed by at least partial removal of a problematic intervertebral disc. The superior component has a superior component top surface with the superior component being placed in the intervertebral space such that the superior component top surface faces the first vertebra or what might remain of a partially removed intervertebral disc. The inferior component has an inferior component bottom surface with the inferior component being placed in the intervertebral space such that the inferior component bottom surface faces the second vertebra or what might remain of a partially removed intervertebral disc. The superior component may have a superior component bottom side and the inferior component may have an inferior component top side which oppose each other when the superior and inferior components are received in the intervertebral space. The superior and inferior components may be in registration with each other when in the intervertebral space and more specifically when the core component is fully inserted between the superior and inferior components as described below.

The core component is configured for insertion between the superior and inferior components. In use, the core component may be inserted between the superior and inferior components when the superior and inferior components have been placed in the intervertebral space, as described above. Upon insertion the core component determines a separation between the superior and inferior components and hence a height of the intervertebral fusion device with the superior component top surface abutting against the first vertebra or what remains of the partially removed intervertebral disc and with the inferior component bottom surface abutting against the second vertebra or what remains of the partially removed intervertebral disc. Differing heights of intervertebral fusion device may be provided by selection from plural core components of different height. Prior to insertion of the core component and the inferior and superior components, the intervertebral space may be further prepared by removal of cartilaginous tissue and by preparation of the exposed vertebral surfaces. Preparation of the exposed vertebral surfaces may include smoothing of the exposed bleeding bone. Alternatively or in addition, the intervertebral space may be prepared through the bone graft conveying aperture in at least one of the inferior and superior components and before insertion of the core component. Alternatively or in addition, the intervertebral space may be prepared through the bone graft material delivery opening after insertion of the core component and before injection of bone graft material. This approach may be more practicable when the bone graft material delivery opening is large, as described below. The latter two approaches may provide for preparation of where bone is to be grown after installation of the intervertebral fusion device and injection of bone graft material. Furthermore, leaving a wider area unprepared may reduce risk of damage and subsidence.

The core component has a core component top surface, a core component bottom surface and a core component side extending therebetween. When the core component is received between the superior and inferior components, a side boundary of the intervertebral fusion device, which extends between the superior component top surface and the inferior component bottom surface and which defines a perimeter of the intervertebral fusion device, is defined by the superior and inferior components and the core component. The side boundary therefore extends completely around the intervertebral fusion device and therefore, for example, constitutes front and back sides and left and right sides when the intervertebral fusion device is of generally cuboidal shape.

The core component defines a bone graft material holding space which is enclosed except at a bone graft material delivery opening and at least one of the core component top and bottom surfaces. A holding space opening in at least one of the core component top and bottom surfaces provides for fluid communication between the bone graft material holding space and the at least one bone graft conveying aperture when the core component is received between the superior and inferior components. When bone graft material in the bone graft material holding space is pressurised, the bone graft material is ejected from the bone graft material holding space through the at least one holding space opening whereby it forms a bridge between the adjacent vertebra and the intervertebral fusion device. Further to this, and depending on circumstances, it may be desirable to fill whatever space there may be between at least one of: the superior component top surface and the first vertebra; and between the inferior component bottom surface and the second vertebra. Opposing faces of adjacent vertebrae are generally concave. Although the superior component top surface and the inferior component bottom surface may be shaped to fit the faces of the adjacent vertebrae, for example by being convex, the superior component top surface and the inferior component bottom surface very rarely abut against the whole of the vertebrae surfaces. Usually, the superior component top surface and the inferior component bottom surface abut against parts of the vertebrae surfaces. Gaps between the superior component top surface and a vertebra surface and between the inferior component bottom surface and a vertebra surface are typical. Ejection of bone graft material through the at least one holding space opening may fill gaps between a vertebrae surface and at least one of the superior component top surface and the inferior component bottom surface and thereby help to promote efficient and robust fusion.

Aside from the advantage conferred when the bone graft material is pressurised, resistance to ejection of bone graft material through the side boundary may also provide for ease of placing of bone graft material in the core component before the intervertebral fusion device is installed between adjacent vertebrae. For example, and according to a first approach, the superior and inferior components may be installed and the bone graft holding space may be packed with bone graft material before the core component is inserted between the superior and inferior components. By way of further example, and according to a second approach, the core component may be inserted between the superior and inferior components and the bone graft holding space may be packed with bone graft material before the thus assembled intervertebral fusion device is installed between adjacent vertebrae. According to either example, and depending on requirements, further bone graft material may or may not be injected into the bone graft holding space by way of the bone graft material injection with the bone graft holding space being or not being pressurised.

The bone graft delivery opening extends through the core component side from outside the side boundary to the bone graft material holding space. The bone graft material delivery opening may be used to fill the bone graft material holding space with bone graft material. Alternatively or in addition, the bone graft material delivery opening may be used to pressurise bone graft material held in the bone graft material holding space. The closure component is configured to close the bone graft material delivery opening, for example after filling of the graft material holding space with bone graft material. As described below, the closure component may be configured to pressurise bone graft material contained in the bone graft material holding space.

The core component engages with each of the superior and inferior components to resist ejection of bone graft material from the bone graft material holding space through the side boundary when the bone graft material delivery opening is closed by the closure component and while bone graft material is ejected through the at least one bone graft conveying aperture. Pressurisation of bone graft material in the bone graft material holding space causes ejection of bone graft material through the at least one bone graft conveying aperture. Engagement of the core component with each of the superior and inferior components presents resistance to ejection of bone graft material through the side boundary and, more specifically, through the side boundary between the core component and the superior component and between the core component and the inferior component. Presenting resistance to ejection of bone graft material in this fashion may maintain pressure within the bone graft material holding space so that bone graft material is ejected through the at least one bone graft conveying aperture. Engagement of the core component with each of the superior and inferior components may be imperfect, for example such that there is no fluid tight seal, whereby air or bone graft material is lost through the side boundary. Nevertheless, engagement of the core component with each of the superior and inferior components present sufficient resistance that bone graft material is ejected preferentially through the at least one bone graft conveying aperture.

A superior bone graft conveying aperture may be defined in the superior component top surface and an inferior bone graft conveying aperture may be defined in the inferior component bottom surface. Bone graft material may therefore be ejected by way of a holding space opening in each of the core component top and bottom surfaces through the superior bone graft conveying aperture and the inferior bone graft conveying aperture.

In an alternative form, a superior bone graft conveying aperture may be defined in the superior component top surface and the inferior component bottom surface may lack an inferior bone graft conveying aperture. Bone graft material may therefore be ejected by way of the holding space opening in the core component top surface and through the superior component only of the superior and inferior components. A gap between a vertebra and the inferior component may be filled before and/or after insertion of the intervertebral fusion device with gravity being relied on to maintain bone graft material in this space.

Resistance to ejection of bone graft material through the side boundary may be by way of the core component contacting each of the superior and inferior components. The core component may contact each of the superior and inferior components around the bone graft holding space. Contact may therefore surround the bone graft receiving space at a respective end of the bone graft receiving space. Contact may thus surround each holding space opening. Contact between the core component and each of the superior and inferior components may not be continuous and absolute around the bone graft holding space. This is because sufficient resistance to ejection through the side boundary may be required for preferential ejection of bone graft material through the at least one bone graft conveying aperture. There may therefore be small gaps in contact between the core component and the superior and inferior components. Furthermore, bone graft material may comprise ceramic or bone chips carried in a binder material. Resistance to ejection through the side boundary may be achieved where gaps in contact between the core component and the superior and inferior components are no larger than the size of the ceramic or bone chips.

Alternatively, and in particular but not exclusively where the bone graft material lacks non-fluid constituents, such as ceramic or bone chips, resistance to ejection of bone graft material through the side boundary may be achieved by sufficient adjacency of the core component to each of the superior and inferior components having regard to viscosity of the bone graft material being used. Where the bone graft material is more viscous, such that it is of the consistency of peanut butter, the core component may be less adjacent to at least one of the superior and inferior components. The bone graft material may have a dynamic viscosity of no more than 250,000 centipoise (cP). Where the bone graft material is less viscous, such that it is of the consistency of saline, greater adjacency of core component and at least one of the superior and inferior components may be needed to maintain pressure of bone graft material such that it is preferentially ejected through the at least one bone graft conveying aperture. The bone graft material may have a dynamic viscosity of at least 0.9 centipoise (cP).

In certain forms of the intervertebral fusion device, the side boundary may define a liquid tight barrier against passage of bone graft material.

The core component may have a core component superior profile, which surrounds the holding space opening, and the superior component may have a superior component profile, the core component superior profile abutting against the superior component profile. The core component superior profile may be substantially planar and the superior component profile may be substantially planar. The core component superior profile may be defined at an edge of a wall of the core component. The edge of the wall may be substantially planar. The wall of the core component may surround and thereby define the bone graft holding space. Furthermore, and where the core component has two holding space openings, an inside surface of the wall may define the bone graft holding space at least in part along the bone graft holding space between the holding space openings.

The core component may have a core component inferior profile, which surrounds the holding space opening, and the inferior component may have an inferior component profile, the core component inferior profile abutting against the inferior component profile. The core component inferior profile may be substantially planar and the inferior component profile may be substantially planar. The core component inferior profile may be defined at an edge of a wall of the core component. The edge of the wall may be substantially planar. The wall of the core component may surround the bone graft holding space. Furthermore, an inside surface of the wall may define the bone graft holding space at least in part along the bone graft holding space between the holding space openings. The wall of the core component defining the core component inferior profile may be the same wall defining the core component superior profile.

As mentioned above, the bone graft material holding space may be defined by an enclosing perimeter wall. The bone graft material delivery opening may extend through the perimeter wall from outside the core component to the bone graft material holding space. The bone graft material holding space as defined by the perimeter wall may be generally rectangular when viewed from one of the holding space openings. Furthermore, a length and a width of the bone graft material holding space may be substantially the same as one progresses from the core component top surface to the core component bottom surface. Where the core component has a holding space opening at each of the component top and bottom surfaces, the enclosing perimeter wall may extend between the holding space opening at the core component top surface and the holding space opening at the core component bottom surface.

A holding space opening may be coterminous with a bone graft material conveying aperture. Where the core component has a holding space opening at each of the component top and bottom surfaces, the holding space opening at the core component top surface may be coterminous with the superior bone graft material conveying aperture and the holding space opening at the core component bottom surface may be coterminous with the inferior bone graft material conveying aperture. Where dimensions of the bone graft material holding space are substantially the same as one progresses from the core component top surface to the core component bottom surface, the superior and inferior bone graft material conveying apertures may be of corresponding extent to the bone graft material holding space.

The superior bone graft material conveying aperture may extend through the superior component whereby the superior bone graft material conveying aperture is open at each of the superior component top surface and a superior component bottom surface of the superior component. The inferior component may be similarly formed. The inferior bone graft material conveying aperture may therefore extend through the inferior component whereby the inferior bone graft material conveying aperture is open at each of the inferior component bottom surface and an inferior component top surface of the inferior component.

The core component may have the form of a wedge and more specifically a frustum of a wedge. The core component and the inferior and superior components may be configured for insertion of the core component to be led by the thinner edge of the thinner and thicker edges of the core component. An inclination of the inferior and superior components relative to each other may thus be determined by way of the core component further to a separation between the inferior and superior components. Extent of inclination of the inferior and superior components may be determined by selection from a plurality of core components having core component top and bottom surfaces different relative inclinations. Nevertheless, the core component engages with each of the superior and inferior components to resist ejection of bone graft material from the bone graft material holding space through the side boundary when the bone graft material delivery opening is closed by the closure component.

The core component may define plural bone graft material delivery openings. The plural bone graft material delivery openings may be closed by the closure component. Alternatively, each of the plural bone graft material delivery openings may be closed by a respective closure component.

The bone graft material delivery opening may be at least 50% of a width of the core component. Alternatively or in addition, the bone graft material delivery opening may be at least 50% of a height of the core component. An area of the bone graft material delivery opening may be at least 60% of an area of an anterior aspect of the core component. Such a large bone graft material delivery opening may provide for ease of introduction of bone graft material to the bone graft material holding space.

The closure component may have a protrusion which is shaped to be received in the bone graft material delivery opening. The protrusion may be a snug fit in the bone graft material delivery opening and more specifically a snap fit in the bone graft material delivery opening. The closure component may further have a base member from which the protrusion extends. The base member may abut against an outside surface of the core component when the protrusion is received in the bone graft material delivery opening.

As described above, bone graft material is ejected through at least one of the inferior and superior components from the bone graft material holding space. The pressure of bone graft material remaining in the bone graft material holding space may decrease as bone graft material is ejected. The core component may be configured to increase the pressure of bone graft material remaining in the bone graft material holding space by reducing an effective volume of the bone graft material holding space. Where the closure component has a protrusion, the closure component may be configured to move the protrusion further into the bone graft material delivery opening to thereby reduce the volume.

In a first form, the closure component may be user operable to move the protrusion further into the bone graft material delivery opening. The protrusion may, for example, be moved on a screw thread which is rotated by the user. The user may thus increase the pressure when he or she notices a drop in the rate of ejection of bone graft material.

In a second form, the protrusion may be self-regulating. According to the second form, the core component may exert a bias and more specifically a spring bias on the protrusion that urges the protrusion further into the bone graft material delivery opening. The protrusion itself may be configured to exert a spring bias. More specifically, the protrusion may comprise a resilient portion of resilient material which deflects upon initial insertion of the protrusion to thereby store energy and in which deflection reduces under exertion of spring bias to thereby reduce the effective volume of the bone graft material holding space. The resilient portion may be a simply supported beam, i.e. a beam supported at or towards both ends.

References herein to anterior or to anterior aspect are to the anterior aspect of the intervertebral fusion device itself and not to the anterior aspect of the patient. The anterior aspect of the intervertebral fusion device itself therefore means the aspect at which the core component is inserted between the superior and inferior components. Correspondingly, references herein to posterior or to posterior aspect are to the posterior aspect of the intervertebral fusion device itself and not to the posterior aspect of the patient. The anterior and posterior aspects are oppositely directed. The intervertebral fusion device may be an anterior, anterior oblique, lateral or direct lateral intervertebral fusion device.

The superior component, the inferior component and the core component may be separate components. Furthermore, the superior component and the inferior component may be disconnected from each other in the absence of the core component. Having separate inferior and superior components and core component and more specifically disconnected inferior and superior components means that the components may be introduced to the intervertebral space more gently compared with known single piece intervertebral fusion devices which often need to be hammered into place. Such a less gentle insertion process may damage the vertebrae and perhaps also the intervertebral fusion device, may increase time required for the intervertebral fusion device to settle in the intervertebral space, and may result in trauma to vertebral bodies, adjacent soft tissues including neural structures. On the subject of trauma, a device that is hammered into place is liable to create microfractures in the vertebrae which could lead to subsidence of the device into the host bone. Furthermore, having separate components and in particular a core component separate to the inferior and superior components allows for differences in dimensions of intervertebral spaces, differences in angle between the adjacent vertebrae that define the intervertebral space, and degree of spinal alignment and/or correction. Each of the superior component, the inferior component and the core component may be integrally formed. The superior component and the inferior component may not engage with each other, other than by way of the core component.

Each of the inferior and superior components may have the form of a plate, albeit a plate having the structures described above thereon that provide for resistance to ejection of bone graft material through the side boundary, whereby it is thin relative to its length and width. At least one of the superior component top side and the inferior component bottom side may be shaped in the coronal or sagittal planes, for example domed, to enhance fit and contact with the adjacent vertebrae.

At least one of the superior component top surface and the inferior component bottom surface may be configured to provide for fusion. For example, the top or bottom side may comprise formations, such as protrusions, which, in use, engage with the bone of the vertebra. By way of another example, the top and/or bottom side may define apertures for passage of bone graft material therethrough from an interior of the intervertebral fusion device. By way of a further example, the top or bottom side may have a coating thereon or impregnation therein. The coating or impregnation may comprise material that provides for bone adhesion and/or bone formation to encourage bone to grow up to and bond onto the intervertebral fusion device to thereby provide long term stable attachment. One or more known coatings may be used, such as porous mesh, tricalcium phosphate (TCP), hydroxyapatite (HA) or bone morphogenetic protein (BMP). At least one of the superior component top surface and the inferior component bottom surface may be configured to provide for cage fixation. Cage fixation may be useful to provide for stability until fusion has taken place.

At least one of the superior component, the core component, the inferior component and the closure component may be formed from a metal, such as titanium, or a metal alloy, such as stainless steel, Ti6Al4V, CoCr or nitinol. Nitinol may be useful in respect of cooperating parts of the superior component, the core component, the inferior component and the closure component. At least one of the superior component, the core component, the inferior component and the closure component may be formed from a plastics material and more specifically a thermoplastic polymer, such as PEEK or carbon reinforced PEEK. In forms of the invention, the core component may be formed in part by 3D printing whereby the core component has the form of a 3D lattice. The aforementioned materials may be used to form the core component by way of 3D printing.

When assembled, the intervertebral fusion device may have a range of length by width from 20 mm by 15 mm to 65 mm by 50 mm. Where there is an oblique intervertebral fusion device, the range of length by width may be from 20 mm by 15 mm to 40 mm by 35 mm. Where there is an anterior intervertebral fusion device, the range of length by width may be from 20 mm by 20 mm to 50 mm by 50 mm. Where there is a lateral intervertebral fusion device, the range of length by width may be from 40 mm by 18 mm to 65 mm by 40 mm. A height of the intervertebral fusion device may be 5 mm to 15 mm at the posterior aspect.

According to a second aspect of the present invention, there is provided a method of installing an intervertebral fusion device in an intervertebral space between first and second adjacent vertebrae, the intervertebral fusion device comprising a superior component having a superior component top surface, an inferior component having an inferior component bottom surface, a core component having a core component top surface, a core component bottom surface and a core component side extending therebetween, and a closure component, a bone graft conveying aperture being defined in at least one of the superior component top surface and the inferior component bottom surface, the method comprising:

positioning the superior component and the inferior component relative to each other;

inserting the core component between the superior and inferior components whereby a separation between the superior and inferior components is determined, a side boundary of the intervertebral fusion device, which extends between the superior component top surface and the inferior component bottom surface and which defines a perimeter of the intervertebral fusion device, being defined by the superior and inferior components and the core component when the core component is received between the superior and inferior components, the core component defining a bone graft material holding space which is enclosed except at at least one of the core component top and bottom surfaces and a bone graft material delivery opening which extends through the core component side from outside the side boundary to the bone graft material holding space, a holding space opening in at least one of the core component top and bottom surfaces providing for fluid communication between the bone graft material holding space and the at least one bone graft conveying aperture when the core component is received between the superior and inferior components;

disposing the intervertebral fusion device in the intervertebral space such that the superior component top surface abuts against the first vertebra and the inferior component bottom surface abuts against the second vertebra;

disposing bone graft material in the bone graft material holding space;

closing the bone graft material delivery opening with the closure component; and pressurising the bone graft material in the bone graft material holding space whereby bone graft material is ejected from the bone graft material holding space through the at least one bone graft conveying aperture in preference to ejection through the side boundary on account of engagement of the core component with each of the superior and inferior components.

The intervertebral fusion device may be installed in an intervertebral space by positioning the superior component and the inferior component relative to each other in the intervertebral space before the core component is inserted between the superior and inferior components. Alternatively, the intervertebral fusion device may be installed in an intervertebral space by positioning the superior component and the inferior component relative to each other at a location apart from the intervertebral space and inserting the core component between the superior and inferior components at this location before the thus assembled intervertebral fusion device is installed in the intervertebral space.

Furthermore, and depending on consistency of the bone graft material, the bone graft material may be disposed at least in part in the bone graft material holding space before the core component is inserted between the inferior and superior components and perhaps also before the intervertebral fusion device is installed in an intervertebral space. The bone graft material may be disposed at least in part in the bone graft material holding space after the core component is inserted between the inferior and superior components and more specifically by injection through the bone graft material delivery opening. Closure of the bone graft material delivery opening with the closure component may pressurise bone graft material in the bone graft material holding space. Alternatively, the bone graft material may be pressurised by the like of a syringe. The like of a syringe may therefore constitute the closure component.

Further embodiments of the second aspect of the present invention may comprise one or more features of the first aspect of the present invention.

BRIEF DESCRIPTION OF DRAWINGS

The present invention will now be described by way of example only with reference to the following drawings, of which.

DESCRIPTION OF EMBODIMENTS

Figure 1A:
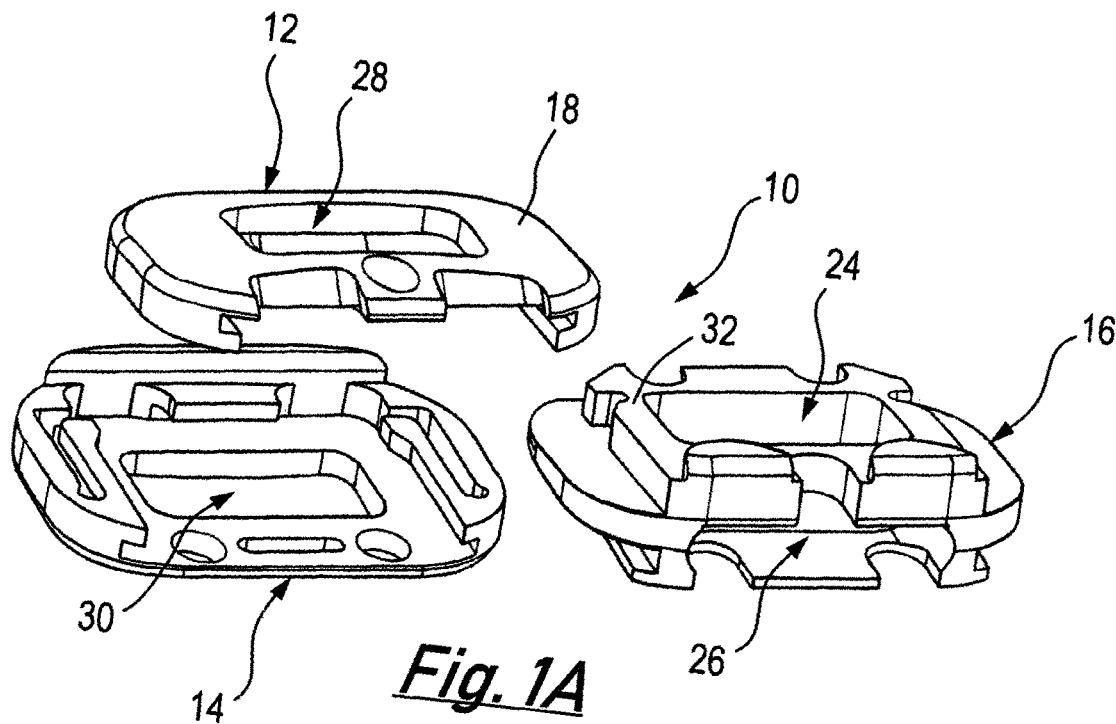
FIG. 1A is an exploded perspective view of an intervertebral fusion device according to an embodiment when viewed from above and one side.
Figure 1B:
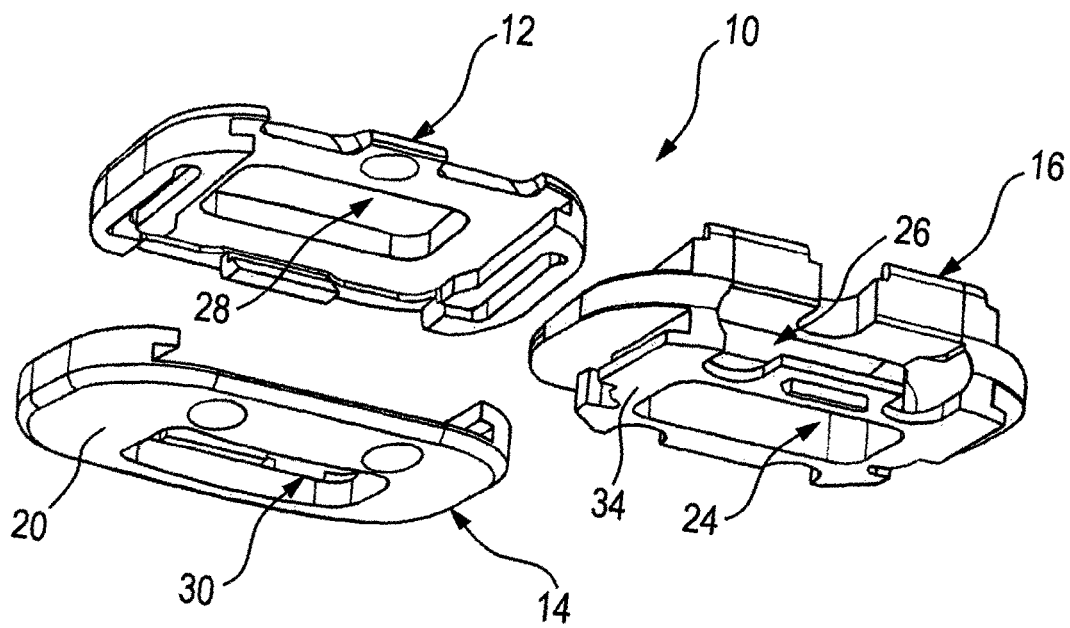
FIG. 1B is an exploded perspective view of the intervertebral fusion device of FIG. 1A when viewed from below and one side.
Figure 2:
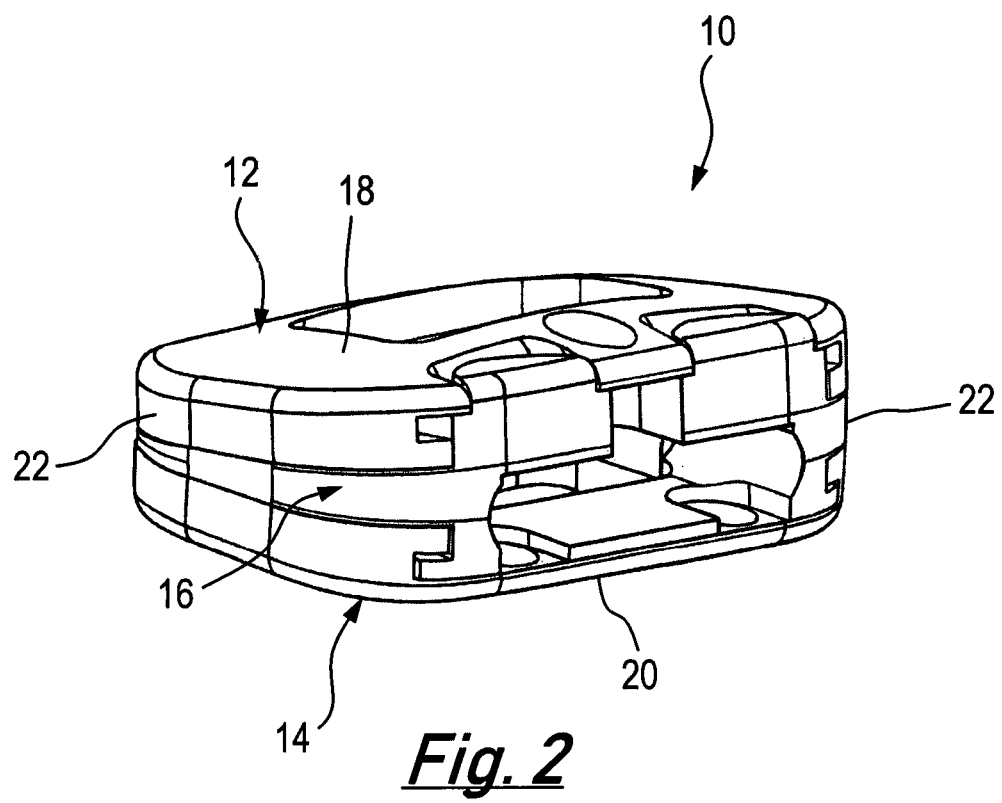
FIG. 2 is perspective view of the intervertebral fusion device of FIGS. 1A and 1B when viewed from above and one side.

FIG. 1A shows an exploded perspective view of an intervertebral fusion device 10 according to an embodiment of the invention when viewed from above, the anterior aspect and one side and FIG. 1B shows an exploded perspective view of the same intervertebral fusion device 10 from below, the anterior aspect and the same side. The intervertebral fusion device 10 is also shown in FIG. 2 when assembled. The intervertebral fusion device 10 comprises a superior component 12, an inferior component 14, a core component 16 and a closure component (not shown in FIGS. 1A, 1B and 2). The closure component is described below with reference to FIGS. 3A and 3B. The superior component 12 has a superior component top surface 18 which, in use, abuts against a first vertebra and the inferior component 14 has an inferior component bottom surface 20 which, in use, abuts against a second vertebra adjacent the first vertebra when the superior and inferior components are placed in the intervertebral space between the first and second vertebrae. The core component 16 is inserted between the thus installed superior and inferior components 12, 14 to thereby determine a separation and angle between the superior and inferior components.

As can be seen from the views of FIGS. 1A and 1B, opposing sides of the superior and inferior components 12, 14 define profiles and the top and the bottom of the core component 16 define profiles. The profiles defined on the top of the core component 16 inter-engage with the profiles defined in the adjacent side of the superior component 12 and the profiles defined on the bottom of the core component 16 inter-engage with the profiles defined in the adjacent side of the inferior component 14 to draw the superior and inferior components tightly to the core component as the core component is inserted. FIG. 2 shows the intervertebral fusion device 10 when the core component 16 is fully inserted between the superior and inferior components 12, 14. A side boundary 22 of the intervertebral fusion device 10, which extends between the superior component top surface 18 and the inferior component bottom surface 20 and which defines a perimeter of the intervertebral fusion device, is defined by the superior and inferior components 12, 14 and the core component 16 when the core component is fully received between the superior and inferior components as shown in FIG. 2.

As can be seen from FIGS. 1A and 1B, the core component 16 defines a bone graft receiving space 24 of generally rectangular cross-section. The bone graft receiving space 24 extends through the core component between a first holding space opening at a top surface of the core component and a second holding space opening at a bottom surface of the core component. A wide bone graft material delivery opening 26 extends from an exterior side of the core component and opens into the bone graft receiving space 24. As described below with reference to FIGS. 3A and 3B, the bone graft material delivery opening 26 is closed by a closure component. The superior component 12 defines a superior bone graft conveying aperture 28 in the superior component top surface 18. The superior bone graft conveying aperture 28 is of substantially the same cross-sectional dimensions as the bone graft receiving space 24. The inferior component 14 defines an inferior bone graft conveying aperture 30 in the inferior component bottom surface 20. The inferior bone graft conveying aperture 30 is of substantially the same cross-sectional dimensions as the bone graft receiving space 24. When the core component 16 is fully received between the superior and inferior component 12, 14 as shown in FIG. 2, the superior bone graft conveying aperture 28 is coterminous with the first holding space opening and the inferior bone graft conveying aperture 30 is coterminous with the second holding space opening. Bone graft material held in the bone graft receiving space 24 can thus be ejected through each of the superior and inferior bone graft conveying apertures 28, 30.

As can be seen from inspection of FIGS. 1A and 1B, the core component has a core component superior profile 32, which surrounds the first holding space opening, and a core component inferior profile 34, which surrounds the first holding space opening. Each edge of the core component superior profile 32 and the core component inferior profile 34 is planar. When the core component 16 is fully inserted between the superior and inferior components 12, 14, as shown in FIG. 2, the planar edge of the core component superior profile 32 abuts against the lower surface of the superior component and the planar edge of the core component inferior profile 34 abuts against the upper surface of the inferior component. The core component and the superior and inferior components are thus configured to present resistance to ejection of bone graft material from the bone graft receiving space 24 between the core component and each of the superior and inferior components through the side boundary 22 of the intervertebral fusion device 10. When bone graft material in the bone graft receiving space 24 is pressurised and when the bone graft material delivery opening 26 is closed, bone graft material is preferentially ejected from the bone graft receiving space through the superior and inferior bone graft conveying apertures 28, 30.

Figure 3A:
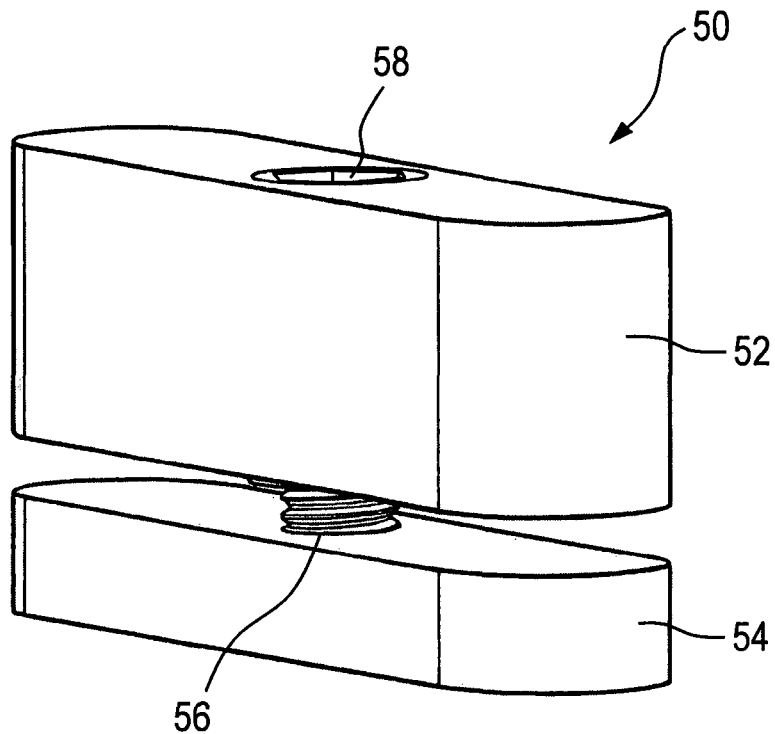
FIG. 3A is a view of a first embodiment of closure component of the intervertebral fusion device.

A view of a first embodiment 50 of closure component of the intervertebral fusion device is shown in FIG. 3A. The closure component 50 is inserted into the bone graft material delivery opening 26. The closure component 50 is a tight fit in the bone graft material delivery opening 26 whereby bone graft material in the core component may be pressurised to sufficient extent without the closure component being ejected. The closure component 50 comprises a base member 52 and a movable member 54. The movable member 54 is received first of the base member and the movable member when the closure component is inserted into the bone graft material delivery opening. The base member 52 and the movable member 54 are mechanically coupled by a threaded bolt 56 which is seated in the base member. The side of the base member 52 facing away from the movable member 54 supports a head 58 of the threaded bolt 56. The user mechanically engages with the head 58 of the threaded bolt, such as with a tool, and rotates the threaded bolt in the base member 52. Rotation of the threaded bolt moves the movable member 54 towards or away from the base member 52 depending on direction of rotation by virtue of cooperation of the thread of the threaded bolt with a thread defined by the movable member. When the user notices that rate of ejection of bone graft material from the bone graft receiving space 24 has dropped, the user rotates the threaded bolt 56 to advance the movable member 54 further towards the bone graft receiving space and away from the base member 52. Pressure in the bone graft receiving space 24 is thus increased to thereby increase the rate of ejection of bone graft material from the bone graft receiving space.

Figure 3B:
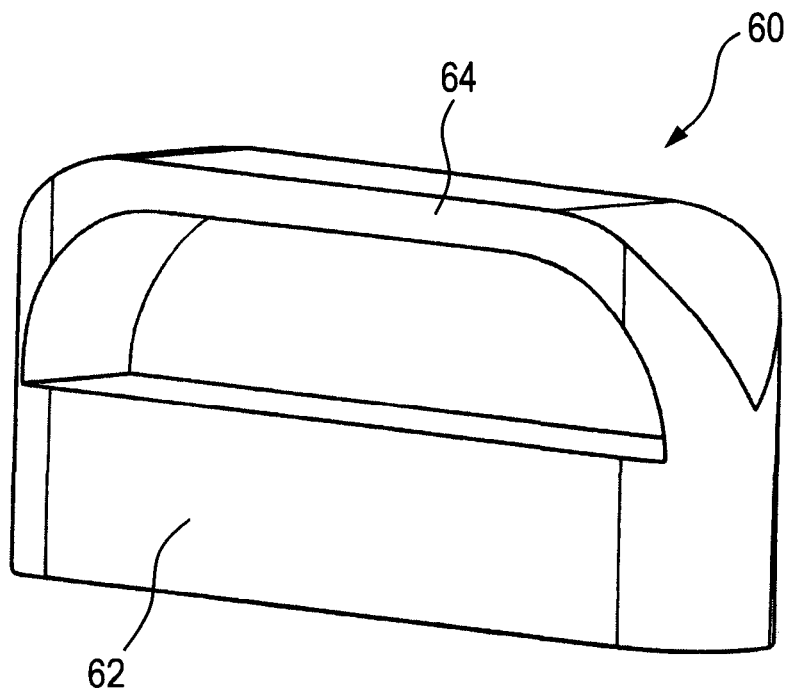
FIG. 3B is a view of a second embodiment of closure component of the intervertebral fusion device.

A view of a second embodiment 60 of closure component of the intervertebral fusion device is shown in FIG. 3B. The second embodiment 60 of closure component operates on a self-regulating basis in contrast to the manually operable first embodiment 50 of closure component. The second embodiment 60 of closure component comprises a base member 62 and a simply supported sprung beam 64 which is supported on an end of the base member. The second embodiment 60 of closure component is inserted with the sprung beam 64 foremost into the bone graft material delivery opening 26. Upon insertion, the sprung beam 64 bows towards the base member 62 and thereby stores energy. The spring bias exerted by the sprung beam 64 into the bone graft receiving space 24 compensates for loss of pressure from the bone graft receiving space as bone graft material is ejected.

The bone graft material held in the bone graft material holding space or injected into the bone graft material holding space has one of three forms. In a first form, the bone graft material consists of bone or ceramic chips carried in a binder such that it has a paste or putty consistency, such as from Surgentec LLC, 7601 N Federal Hwy, Suite 150A, Boca Raton, FL 33487, USA or from Pinnacle Spine Group, 2921 Canton Street, Dallas, TX 75226, USA. In a second form, the bone graft material consists of viscous fluid, such as from Zimmer Biomet Dental, 4555 Riverside Drive, Palm Beach Gardens, FL 33410, USA or from Dentsply Sirona, Susquehanna Commerce Center, 221 W. Philadelphia Street, Suite 60W, York, PA 17401, USA. In a third form, the bone graft material consists of bone or ceramic chips only, i.e. no carrier material present although typically mixed with bone marrow aspirate or blood, such as from Kleiner Device Labs, LLC, 999 Driver Way, Incline Village, NV 89451, USA.

Figure 4:
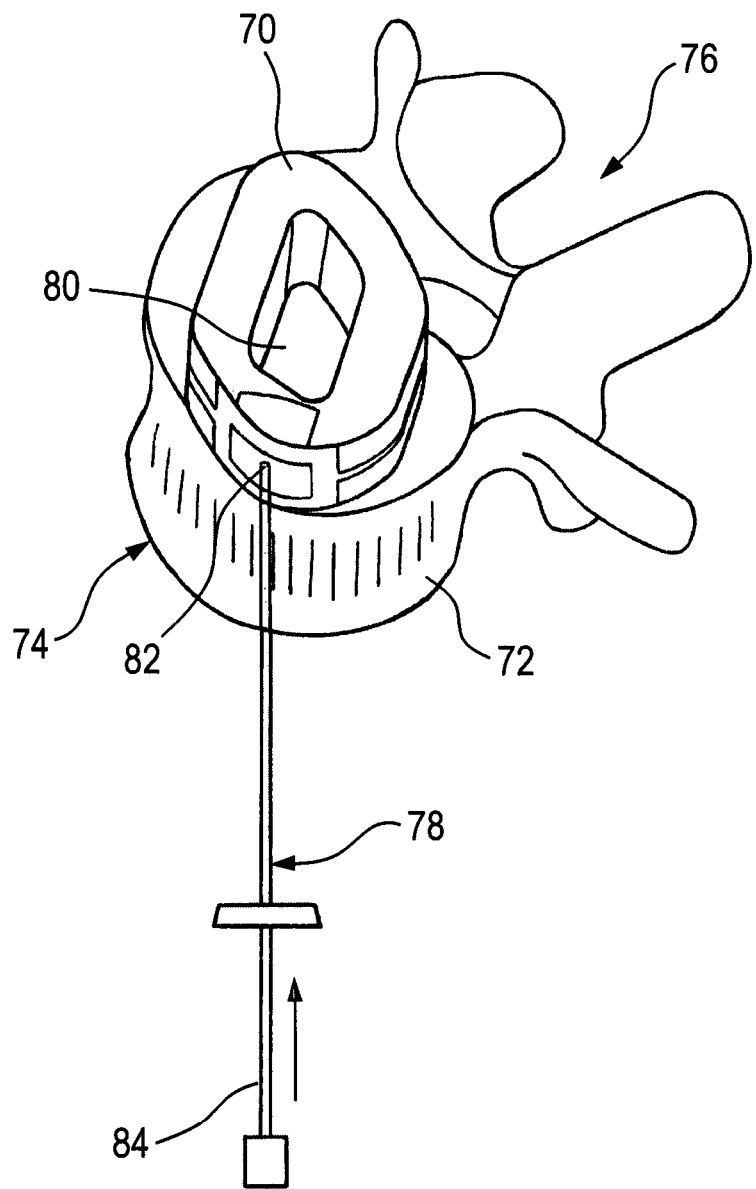
FIG. 4 is a view of an intervertebral fusion device according to another embodiment in situ and while bone graft material is being injected.

FIG. 4 shows another embodiment of intervertebral fusion device 70 in place above a lower vertebra 72. The lower vertebra 70 has an anatomical anterior aspect 74 and an anatomical posterior aspect 76. For illustrative purposes, the adjacent upper vertebra is not shown in FIG. 4. The embodiment of FIG. 4 is an oblique lateral interbody fusion device. The shape of the embodiment of FIG. 4 is therefore different such that the anterior aspect of the device is presented at an angle to a line between the anterior and posterior anatomical aspects. Nevertheless, the embodiment of FIG. 4 has the same configuration as the embodiment 10 of FIGS. 1A to 3 such that the core component engages with each of the superior and inferior components to resist ejection of bone graft material from the bone graft material holding space through the side boundary when the bone graft material delivery opening is closed by the closure component and while bone graft material is ejected through the inferior and the superior bone graft conveying apertures.

As shown in FIG. 4, a plunger device 78 is used to inject bone graft material into the bone graft material holding space 80. A distal end 82 of the plunger device 78 is inserted into the bone graft material delivery opening and a plunger 84 of the plunger device 78 is depressed to inject bone graft material into the bone graft material holding space 80 from the plunger device. When sufficient bone graft material has been injected, the distal end 82 of the plunger device is withdrawn from the bone graft material delivery opening and the bone graft material delivery opening is closed with a closure component, such as of the form shown in FIG. 3A or 3B.

The plunger device 78 is used to inject bone graft material of the second form described above. If the bone graft material of the first form is of relatively low viscosity, the plunger device 78 can be used for injection of the bone graft material. Alternatively, bone graft material of the first form is packed into the bone graft material holding space by way of the bone graft material delivery opening. As mentioned above, bone graft material can be placed in the bone graft material holding space before the intervertebral fusion device is placed in assembled form in the intervertebral space, subject to the bone graft material being sufficiently viscous. Further to this, and if the need arises, further bone graft material is injected into the bone graft material holding space when the intervertebral fusion device is in situ. Bone graft material of the third form is introduced into the intervertebral fusion device when in situ by way of the like of a funnel placed in the bone graft material delivery opening. The thus introduced bone graft material is then packed tightly with a tamp. Irrespective of the form of the bone graft material and whether the bone graft material is placed in the bone graft material holding space before installation or is injected or packed after installation, engagement of the core component with each of the superior and inferior components resists ejection of the thus held bone graft material through the side boundary 22.

The invention claimed is:

1. An intervertebral fusion implant comprising:
a superior component configured to be received in an intervertebral space between first and second vertebrae whereby a superior component top surface of the superior component is configured to abut against the first vertebra;
an inferior component configured to be received in the intervertebral space whereby an inferior component bottom surface of the inferior component is configured to abut against the second vertebra, a bone graft conveying aperture defined in at least one of the superior component top surface and the inferior component bottom surface;
a core component having a core component top surface, a core component bottom surface and a core component side extending therebetween, the core component configured to be received between the superior and inferior components to determine a separation therebetween, a side boundary of the intervertebral fusion implant, which extends between the superior component top surface and the inferior component bottom surface and which defines a perimeter of the intervertebral fusion implant, defined by the superior and inferior components and the core component when the core component is received between the superior and inferior components; and
a closure component, wherein:
the core component defines a bone graft material holding space which is enclosed except at a bone graft material delivery opening in the core component side and at at least one of the core component top and bottom surfaces, a holding space opening in at least one of the core component top and bottom surfaces providing for fluid communication between the bone graft material holding space and the bone graft conveying aperture defined in at least one of the superior component top surface and the inferior component bottom surface when the core component is received between the superior and inferior components;
the bone graft material delivery opening extends through the core component side from the side boundary to the bone graft material holding space, the closure component configured to close the bone graft material delivery opening;

the core component engages with each of the superior and inferior components to resist ejection of bone graft material from the bone graft material holding space through the side boundary when the bone graft material delivery opening is closed by the closure component and while bone graft material is ejected through the bone graft conveying aperture defined in at least one of the superior component top surface and the inferior component bottom surface; and the superior component, the inferior component and the core component are separate components, and the superior component and the inferior component do not engage with each other than by way of the core component.

2. The intervertebral fusion implant according to claim 1, wherein a superior bone graft conveying aperture is defined in the superior component top surface and an inferior bone graft conveying aperture is defined in the inferior component bottom surface, wherein the core component comprises a holding space opening in each of the core component top and bottom surfaces, whereby bone graft material is ejectable by way of the holding space opening in each of the core component top and bottom surfaces through the superior bone graft conveying aperture and through the inferior bone graft conveying aperture.

3. The intervertebral fusion implant according to claim 1, wherein the bone graft conveying aperture is a superior bone graft conveying aperture defined in the superior component top surface and the inferior component bottom surface lacks a bone graft conveying aperture, wherein the core component defines a holding space opening in the core component top surface, whereby bone graft material is ejectable by way of the holding space opening in the core component top surface and thereby through the superior component only of the superior and inferior components.

4. The intervertebral fusion implant according to claim 1, wherein the core component contacts each of the superior and inferior components to present resistance to ejection of bone graft material through the side boundary.

5. The intervertebral fusion implant according to claim 4, wherein the core component contacts each of the superior and inferior components around the bone graft material holding space whereby contact between the core component and the superior component encircles the bone graft material holding space at a superior component end of the bone graft material holding space and contact between the core component and the inferior component encircles the bone graft material holding space at an opposite, inferior component end of the bone graft material holding space.

6. The intervertebral fusion implant according to claim 5, wherein contact between the core component and each of the superior and inferior components is not continuous around the bone graft material holding space but is sufficient to present resistance to ejection of bone graft material through the side boundary whereby bone graft material is preferentially ejected through the bone graft conveying aperture defined in at least one of the superior component top surface and the inferior component bottom surface.

7. A kit of parts for intervertebral fusion comprising the intervertebral fusion implant according to claim 6, and further comprising bone graft material, the bone graft material comprising plural ceramic or bone chips carried in a binder material, wherein there are gaps in contact between the core component and the superior and inferior components, and wherein each gap is no larger than the size of a ceramic or bone chip.

8. A kit of parts for intervertebral fusion comprising the intervertebral fusion implant according to claim 1, and further comprising bone graft material, wherein the core component is adjacent each of the superior and inferior components around the bone graft material holding space whereby the bone graft material holding space is encircled at a respective end of the bone graft material holding space, wherein the core component is not in contact with at least one of the superior and inferior components at at least one location where the core component is adjacent the superior component or inferior component, and wherein the bone graft material has a dynamic viscosity of at least 0.9 centipoise (cP) to thereby present resistance to ejection of bone graft material through the side boundary.

9. The intervertebral fusion implant according to claim 1, wherein the side boundary defines a liquid tight barrier against passage of bone graft material.

10. The intervertebral fusion implant according to claim 1, wherein the core component has a core component superior profile, which encircles the holding space opening, and wherein the superior component has a superior component profile, the core component superior profile abutting against the superior component profile.

11. The intervertebral fusion implant according to claim 10, wherein the core component superior profile is substantially planar and the superior component profile is substantially planar.

12. The intervertebral fusion implant according to claim 10, wherein the core component superior profile is defined at an edge of a wall of the core component, the wall of the core component encircling and thereby defining an end of the bone graft material holding space.

13. The intervertebral fusion implant according to claim 12, wherein there is a holding space opening in each of the core component top and bottom surfaces, an inside surface of the wall of the core component defining the bone graft material holding space between the holding space openings.

14. The intervertebral fusion implant according to claim 1, wherein a bone graft material conveying aperture defined in the superior component top surface extends through the superior component whereby the superior bone graft material conveying aperture is open at each of the superior component top surface and a superior component bottom surface of the superior component.

15. The intervertebral fusion implant according to claim 1, wherein a bone graft material conveying aperture defined in the inferior component bottom surface extends through the inferior component whereby the inferior bone graft material conveying aperture is open at each of the inferior component bottom surface and an inferior component top surface of the inferior component.

16. The intervertebral fusion implant according to claim 1, wherein the closure component comprises a base component and a protrusion, the protrusion shaped to be a snug fit in the bone graft material delivery opening, and wherein the core component is configured to increase pressure of bone graft material remaining in the bone graft material holding space after ejection of bone graft material through at least one of the inferior and superior components by reducing an effective volume of the bone graft material holding space, the effective volume reduced by movement of the protrusion further into the bone graft material delivery opening and relative to the base component.

17. The intervertebral fusion implant according to claim 16, wherein the closure component is user operable to move the protrusion further into the bone graft material delivery opening and relative to the base component.

18. The intervertebral fusion implant according to claim 16, wherein the base component exerts a spring bias on the protrusion to urge the protrusion away from the base component and further into the bone graft material delivery opening.

19. The intervertebral fusion implant according to claim 1, wherein the bone graft material delivery opening is at one of an anterior aspect and a posterior aspect of the core component, the other one of the anterior aspect and the posterior aspect having no bone graft material delivery opening.

20. The intervertebral fusion implant according to claim 1, wherein the bone graft material holding space defined by the core component is surrounded on all sides except at the bone graft material delivery opening in the core component side and at at least one of the core component top and bottom surfaces.

21. A method of installing an intervertebral fusion implant in an intervertebral space between first and second adjacent vertebrae, the intervertebral fusion implant comprising a superior component having a superior component top surface, an inferior component having an inferior component bottom surface, a core component having a core component top surface, a core component bottom surface and a core component side extending therebetween, and a closure component, a bone graft conveying aperture defined in at least one of the superior component top surface and the inferior component bottom surface, the method comprising:
  positioning the superior component and the inferior component relative to each other;
  inserting the core component between the superior and inferior components whereby a separation between the superior and inferior components is determined, a side boundary of the intervertebral fusion implant, which extends between the superior component top surface and the inferior component bottom surface and which defines a perimeter of the intervertebral fusion implant, defined by the superior and inferior components and the core component when the core component is received between the superior and inferior components, the core component defining a bone graft material holding space which is enclosed except at a bone graft material delivery opening in the core component side and at at least one of the core component top and bottom surfaces, the bone graft material delivery opening extending through the core component side from the side boundary to the bone graft material holding space, a holding space opening in at least one of the core component top and bottom surfaces providing for fluid communication between the bone graft material holding space and the bone graft conveying aperture defined in at least one of the superior component top surface and the inferior component surface when the core component bottom is received between the superior and inferior components;
  disposing the intervertebral fusion implant in the intervertebral space such that the superior component top surface abuts against the first vertebra and the inferior component bottom surface abuts against the second vertebra;
  disposing bone graft material in the bone graft material holding space;
  closing the bone graft material delivery opening with the closure component; and
  pressurising the bone graft material in the bone graft material holding space whereby bone graft material is ejected from the bone graft material holding space through the bone graft conveying aperture defined in at least one of the superior component top surface and the inferior component bottom surface and ejection of bone graft material through the side boundary is resisted on account of engagement of the core component with each of the superior and inferior components, wherein the superior component, the inferior component and the core component are separate components, and the superior component and the inferior component do not engage with each other than by way of the core component.

22. The method of installing an intervertebral fusion implant according to claim 21, wherein the superior and inferior components are positioned relative to each other in the intervertebral space before the core component is inserted between the superior and inferior components.

* * * * *